(12) United States Patent
Kitagawa

(10) Patent No.: US 9,696,532 B2
(45) Date of Patent: Jul. 4, 2017

(54) SCANNING LASER MICROSCOPE

(71) Applicant: OLYMPUS CORPORATION, Shibuya-ku, Tokyo (JP)

(72) Inventor: Hisao Kitagawa, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 14/560,963

(22) Filed: Dec. 4, 2014

(65) Prior Publication Data

US 2015/0205086 A1 Jul. 23, 2015

(30) Foreign Application Priority Data

Jan. 21, 2014 (JP) .................................. 2014-008573

(51) Int. Cl.
*G02B 21/00* (2006.01)
*G02B 21/16* (2006.01)
*G01N 21/64* (2006.01)

(52) U.S. Cl.
CPC ....... *G02B 21/002* (2013.01); *G01N 21/6458* (2013.01); *G02B 21/16* (2013.01); *G01N 2021/6419* (2013.01)

(58) Field of Classification Search
CPC .. G02B 21/002; G02B 21/16; G01N 21/6458; G01N 2021/6419
USPC ........................................... 250/458.1, 459.1
See application file for complete search history.

(56) References Cited

U.S. PATENT DOCUMENTS

| 4,289,400 | A | * | 9/1981 | Kubota | G01B 11/255 356/445 |
| 6,051,835 | A | * | 4/2000 | Pettipiece | G01J 3/2823 250/339.09 |
| 6,603,537 | B1 | * | 8/2003 | Dietz | G01N 15/1475 250/458.1 |
| 2007/0253044 | A1 | * | 11/2007 | Steinert | G02B 7/004 359/810 |
| 2012/0248292 | A1 | * | 10/2012 | Ozcan | G02B 21/00 250/208.1 |
| 2012/0313012 | A1 | * | 12/2012 | Selvin | G06T 3/4069 250/459.1 |
| 2013/0015370 | A1 | * | 1/2013 | Damaskinos | G01N 21/6452 250/459.1 |

(Continued)

OTHER PUBLICATIONS

Claus B. Muller, et al, "Image Scanning Microscopy", Physical Review Letters 104, 2010, pp. 198101-1 to 198101-4.

*Primary Examiner* — David Porta
*Assistant Examiner* — Gisselle Gutierrez
(74) *Attorney, Agent, or Firm* — Holtz, Holtz & Volek PC

(57) ABSTRACT

An image having an expected superresolution effect is created in a straightforward manner and with superior precision. The invention provides a scanning laser microscope including a scanner that scans a laser beam emitted from an Ar laser device on a specimen; an objective lens that radiates the laser beam scanned by the scanner onto the specimen and that collects return light coming from the specimen; a detector array that has a plurality of minute detector elements arrayed at a position that is optically conjugate with the focal position of the objective lens; and a superresolution calculating portion that calculates a center position of a spot of the return light that is incident on the detector array on the basis of a light intensity signal output from each of the minute detector elements in the detector array.

3 Claims, 5 Drawing Sheets

(56) References Cited

U.S. PATENT DOCUMENTS

| | | | | |
|---|---|---|---|---|
| 2013/0027518 A1* | 1/2013 | MacKay | ............... | G02B 21/26 348/46 |
| 2013/0155499 A1* | 6/2013 | Dixon | ................. | G02B 21/002 359/385 |
| 2014/0063194 A1* | 3/2014 | Zhuang | ............. | G01N 21/6428 348/46 |
| 2015/0004637 A1* | 1/2015 | Cohen | ................ | G02B 21/0076 435/29 |
| 2015/0053870 A1* | 2/2015 | Rumyantsev | ...... | G01N 21/6458 250/459.1 |
| 2015/0177149 A1* | 6/2015 | Yang | ................. | G02B 21/0024 250/459.1 |
| 2015/0226539 A1* | 8/2015 | Roeth | ................. | G01B 11/005 356/614 |
| 2015/0241351 A1* | 8/2015 | Cooper | ............. | G01N 21/6458 250/459.1 |
| 2015/0260978 A1* | 9/2015 | Cremer | ............. | G02B 21/0004 348/79 |

\* cited by examiner

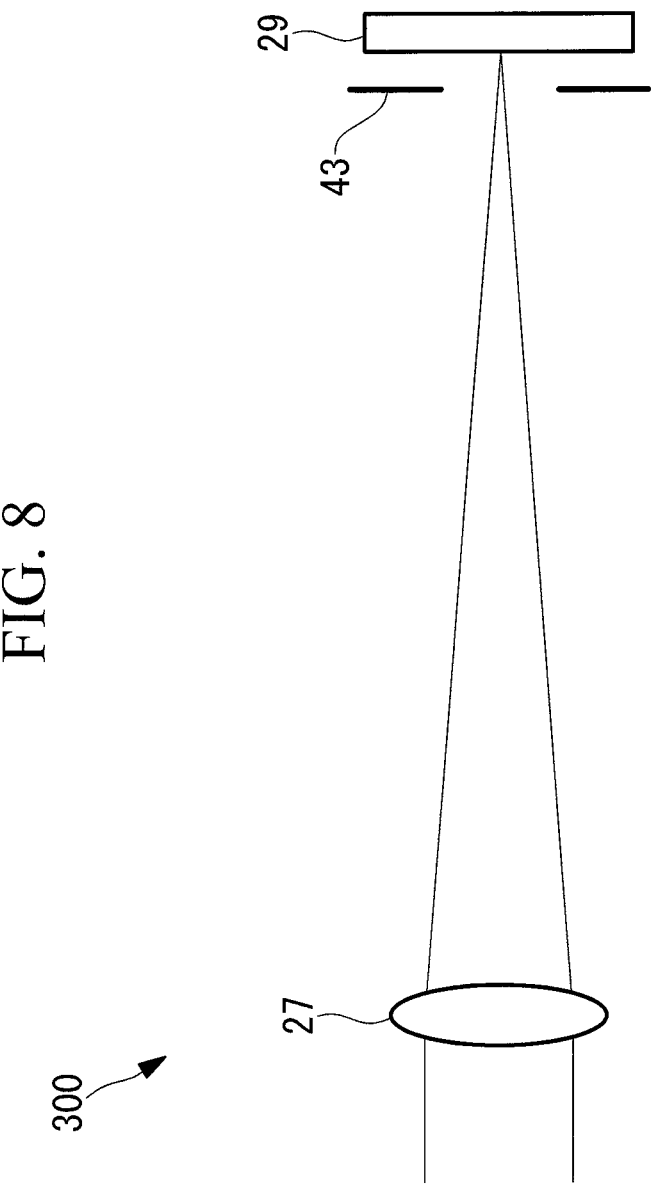

SCANNING LASER MICROSCOPE

CROSS-REFERENCE TO RELATED APPLICATIONS

This application is based on Japanese Patent Application No. 2014-008573, the contents of which are incorporated herein by reference.

TECHNICAL FIELD

The present invention relates to a scanning laser microscope.

BACKGROUND ART

Since the deciphering of the human genome, the biological behavior of individual cells, such as the pathogenesis of cancer and the like, the mechanisms of embryogenesis/specialization of individual organs like the heart and cranial nerves, and so on, are being unraveled at the molecular level. Thus, when examining biological samples such as cells by using microscopes, there is a demand to observe the behavior at the level of individual biological molecules, such as proteins, DNA/RNA, and so forth. To achieve this, super-resolution observation that exceeds optical resolution is becoming increasingly important.

In the related art, there is a known technique for obtaining an image with a resolution exceeding the diffraction limit (superresolution) by using a detector formed of a plurality of detector elements, such as a CCD or PMT array (for example, see Non Patent Literature 1). In the technique described in Non Patent Literature 1, a two-dimensional detector array is disposed at a position conjugate with the focal position of an objective lens, and a spot of return light coming from a laser beam spot scanned on a specimen by means of a scanner is subdivided and detected by the plurality of detector elements.

Then, a superresolution image of the specimen is created by arraying, in association with the scanning position of the scanner, pixel values obtained by summing light intensity signals of the return light coming from the same position on the specimen, which are detected by different detector elements at different detection timings in accordance with the laser beam scanning.

CITATION LIST

Non Patent Literature

{NPL 1}
"Image Scanning Microscopy", Physical Review Letters 104, 198101 (2010), http://dx.doi.org/10.1103/PhysRevLett.104.198101

SUMMARY OF INVENTION

Technical Problem

To achieve a superresolution effect via the technique described in Non Patent Literature 1, it is necessary to make the position of the spot of return light that is incident on the two-dimensional detector array coincident with the positions of the individual detector elements. In the technique described in Non Patent Literature 1, if the positional relationship between the spot of return light and the individual detector elements becomes misaligned, image formation cannot be performed correctly.

The present invention provides a scanning laser microscope that can easily and precisely create an image having the expected superresolution effect.

Solution to Problem

An aspect of the present invention is a scanning laser microscope including a scanning portion that scans a laser beam emitted from a light source on a specimen; an objective lens that radiates the laser beam scanned by the scanning portion onto the specimen and that collects return light coming from the specimen; a detector portion that has a plurality of detector elements arrayed at a position that is optically conjugate with the focal position of the objective lens; and a calculating portion that calculates a center position of a spot of the return light that is incident on the detector portion on the basis of a light intensity signal output from each of the detector elements in the detector portion.

With this aspect, the laser beam emitted from the light source is scanned by the scanning portion and is radiated onto the specimen by the objective lens. Also, the return light returning from the laser beam spot on the specimen is collected by the objective lens and is incident on the detector portion, and the spot of return light is subdivided and detected by the plurality of detector elements. Therefore, it is possible to create a superresolution image of the specimen by arraying, in association with the scanning position of the scanning portion, pixel values obtained by summing light intensity signals of the return light coming from the same position on the specimen, which are detected by different detector elements at different detection timings according to the scanning of the laser beam.

Then, because the center position of the spot of return light is calculated by the calculating portion, if the spot of return light and the detector portion are moved relative to each other so that the center position of the spot of return light is aligned with the center position of the detector portion, it is possible to positionally align the spot of return light and the detector elements of the detector portion in a straightforward manner.

Accordingly, even if the positional relationship of the spot of return light and the detector elements becomes misaligned, it is possible to easily align the position of the spot of return light and the position of the detector elements, and it is thus possible to create an image having the expected superresolution effect in a straightforward manner and with superior precision.

In the above-described aspect, the calculating portion may compare outputs from the detector elements and determine that a center position of the spot of the return light is disposed at a detector element where the intensity of the return light is highest.

The intensity of the return light tends to be stronger closer to the center of the spot. Therefore, by regarding the spot of return light as being located at the detector element where the strongest return light is detected, it is possible to easily calculate the center position of the spot of return light.

The above-described aspect may further include a controller that moves the detector portion or a selection range of the detector elements so that the center position of the spot, which is calculated by the calculating portion, is aligned with the center position of the detector portion.

With this configuration, even if the positional relationship between the spot of return light and the plurality of detector elements becomes misaligned, the spot of return light and the detector elements of the detector portion can be automatically positionally aligned by the controller.

The above-described aspect may further include a controller that moves an incident position of the spot of return light on the detector portion so that the center position of the spot, which is calculated by the calculating portion, is aligned with the center position of the detector portion.

With this configuration, even if the positional relationship of the spot of return light and the plurality of detector elements becomes misaligned, the spot of return light and the detector elements of the detector portion can be automatically positionally aligned by the controller.

The above-described aspect may further include a parallel-sided flat glass plate that can move the spot of the return light incident on the detector portion in accordance with an angle thereof, wherein the controller may change the angle of the parallel-sided flat glass plate.

With this configuration, the spot of return light incident on the detector portion is moved simply by changing the angle of the parallel-sided flat glass plate with the controller, and it is thus possible to align the center position of the spot of return light and the center position of the detector portion in a straightforward manner.

In the above-described aspect, the detector portion may have an odd number×odd number of the detector elements.

With this configuration, by two-dimensionally disposing the detector elements with any one of the detector elements at the center, it is possible to align the center of the spot of return light with the single detector element located at the center of the detector portion. Accordingly, it is possible to obtain a higher-precision intensity signal corresponding to the brightness of the return light.

In the above-described aspect, in a case where the objective lens or the wavelength of the laser beam changes, the calculating portion may calculate the center position of the spot of the return light.

There are situations where, when the objective lens or the laser beam wavelength is changed, the positional relationship between the spot of return light and the detector elements becomes misaligned; however, with this configuration, if the objective lens or the laser beam wavelength is changed, the center position of the spot of return light is automatically calculated by the calculating portion, and the position of the spot of return light and the position of the detector elements of the detector portion can be aligned by the controller. Accordingly, it is possible to create an image having the expected superresolution effect in a straightforward manner and with superior precision with the changed objective lens or laser beam wavelength.

Advantageous Effects of Invention

The present invention affords an advantage in that an image having the expected superresolution effect can be created easily and with superior precision.

BRIEF DESCRIPTION OF DRAWINGS

FIG. 8 is a diagram showing an aperture in a scanning laser microscope according to a modification of the third embodiment of the present invention.

DESCRIPTION OF EMBODIMENTS

First Embodiment

A scanning laser microscope according to a first embodiment of the present invention will be described below with reference to the drawings.

Figure 1:
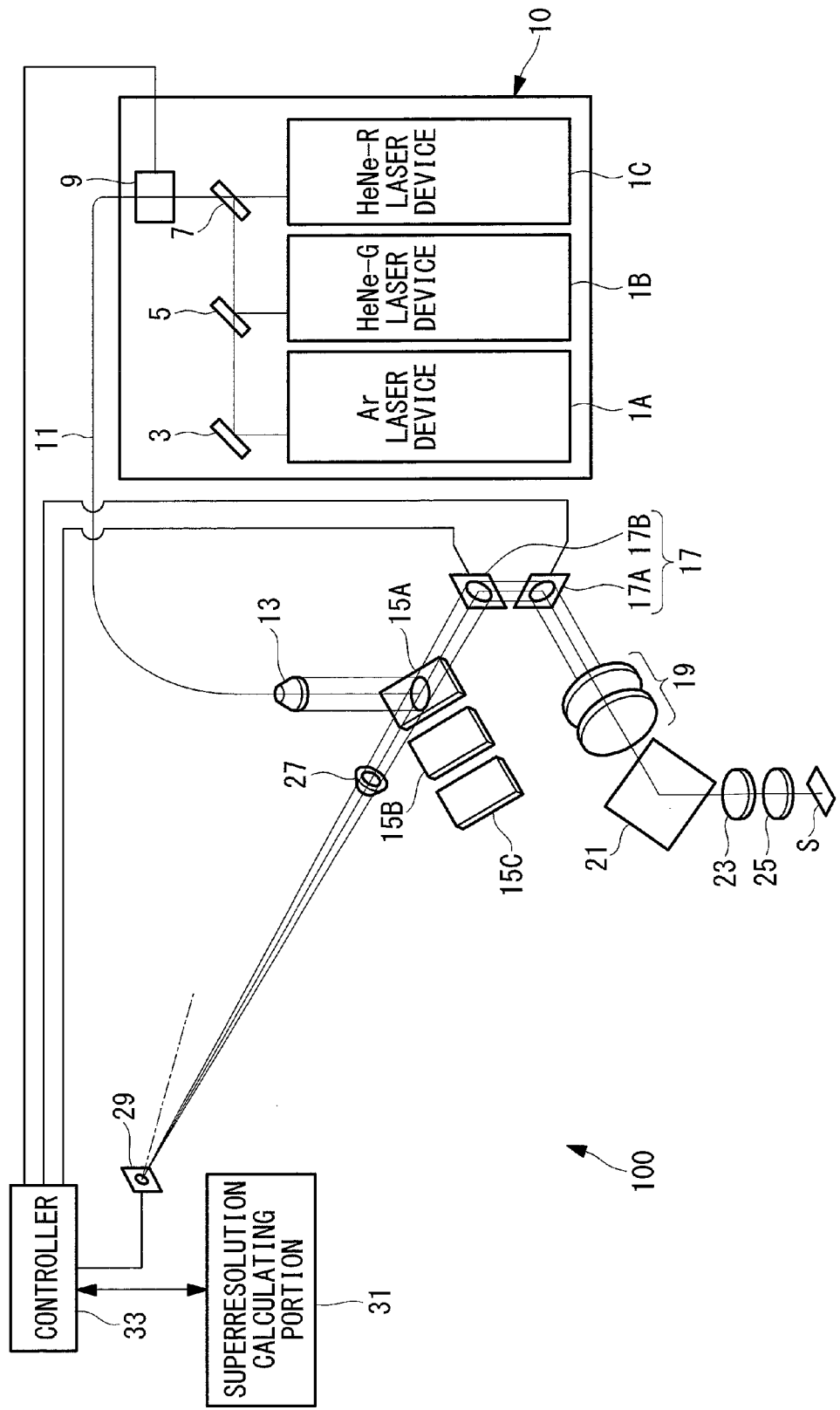
FIG. 1 is a schematic diagram showing the configuration of a scanning laser microscope according to a first embodiment of the present invention.

As shown in FIG. 1, a scanning laser microscope 100 according to this embodiment includes a laser unit 10 that generates a laser beam; a single-mode fiber 11 that guides the laser beam emitted from the laser unit 10; a collimator lens 13 that shapes the laser beam guided by the single-mode fiber 11 into a collimated beam; three excitation dichroic mirrors 15A, 15B, and 15C that can reflect the laser beam shaped into a collimated beam; a galvanometer scanner (scanning portion) 17 that deflects the laser beam reflected by one of the excitation dichroic mirrors 15A, 15B, and 15C; a pupil projection lens 19 that relays the deflected laser beam; a reflecting mirror 21 that reflects the relayed laser beam; an image-forming lens 23 that forms an image by focusing the laser beam reflected by the reflecting mirror 21; and an objective lens 25 that irradiates a specimen S with the laser beam focused by the image-forming lens 23 and that also collects fluorescence generated in the specimen S.

The scanning laser microscope 100 also includes a confocal lens 27 that focuses fluorescence that is collected by the objective lens 25, that returns along the light path of the laser beam, that is descanned by the galvanometer scanner 17, and that passes through the excitation dichroic mirror 15A, 15B, or 15C in the light path; a detector array (detector portion) 29 that detects the fluorescence focused by the confocal lens 27; a superresolution calculating portion (calculating portion) 31 that performs computational processing on the light intensity signals obtained by the detector array 29; and a controller 33 that controls an acousto-optic element 9, the galvanometer scanner 17, and the detector array 29.

The laser unit 10 can output, to a specimen S that is stained with a fluorescent dye, individual laser beams having excitation wavelengths for that fluorescent dye. This laser unit 10 includes, for example, an Ar laser device (light source) 1A that generates a laser beam having an excitation wavelength of 488 nm, a HeNe-G laser device (light source) 1B that generates a laser beam having an excitation wavelength of 543 nm, and a HeNe—R laser device (light source) 1C that generates a laser beam having an excitation wavelength of 633 nm.

The laser unit 10 includes a reflecting mirror 3 that reflects the laser beam emitted from the Ar laser device 1A; a dichroic mirror 5 that combines laser beams of two wavelengths, that is, the wavelength of 488 nm and the wavelength of 543 nm; a dichroic mirror 7 that combines laser beams of three wavelengths, that is, the wavelength of 488 nm, the wavelength of 543 nm, and the wavelength of 633 nm; and the acousto-optic element (AOTF) 9 that selects any laser beam from among the wavelengths of 488 nm, 543 nm, and 633 nm.

The three excitation dichroic mirrors 15A, 15B, and 15C are disposed, in a manner allowing them to be selectively inserted/removed, in the light path of the laser beam that has passed through the collimator lens 13. These three excitation dichroic mirrors 15A, 15B, and 15C have the property that they reflect the respective laser beams coming from the collimator lens 13 and transmit the fluorescence coming from the specimen S.

Specifically, the excitation dichroic mirror 15A is configured so as to reflect the laser beams with the excitation wavelengths of 488 nm, 543 nm, and 633 nm and to transmit fluorescence from the specimen S excited by these laser beams. The excitation dichroic mirror 15B is configured so as to reflect the laser beam with the excitation wavelength of 488 nm and to transmit light with wavelengths longer than the excitation wavelength of 488 nm. The excitation dichroic mirror 15C is configured so as to reflect the laser beam with the excitation wavelength of 543 nm and to transmit light with wavelengths longer than the excitation wavelength of 543 nm.

These excitation dichroic mirrors 15A, 15B, and 15C are selectively used depending on the type of specimen S to be observed. For example, when performing fluorescence observation using only the laser beam with the excitation wavelength of 633 nm and when performing multi-fluorescence observation using multiple excitation wavelengths, the excitation dichroic mirror 15A is used. When performing fluorescence observation using only the laser beam with the excitation wavelength of 488 nm, the excitation dichroic mirror 15B is used. When performing fluorescence observation using only the laser beam with the excitation wavelength of 543 nm, the excitation dichroic mirror 15C is used. By doing so, the fluorescence collection efficiency can be improved.

The galvanometer scanner 17 is provided with a pair of mirrors including an X galvanometer mirror (scanning member) 17A and a Y galvanometer mirror (scanning member) 17B that can swivel about mutually orthogonal swivel axes. The X galvanometer mirror 17A is configured to scan the laser beam in the horizontal direction, and the Y galvanometer mirror 17B is configured to scan the laser beam in the vertical direction.

The X and Y galvanometer mirrors 17A and 17B are disposed in the reflected-light path of the laser beam reflected by the excitation dichroic mirror 15A, 15B, or 15C, and are configured so that the laser beams with the excitation wavelengths of 488 nm, 543 nm, and 633 nm can be two-dimensionally scanned (in the X-direction and the Y-direction) on the specimen S.

The confocal lens 27 is configured to form an image by focusing the fluorescence from the excitation dichroic mirror 15A, 15B, or 15C and to project a confocal spot of the fluorescence on the detector array 29.

Figure 2:
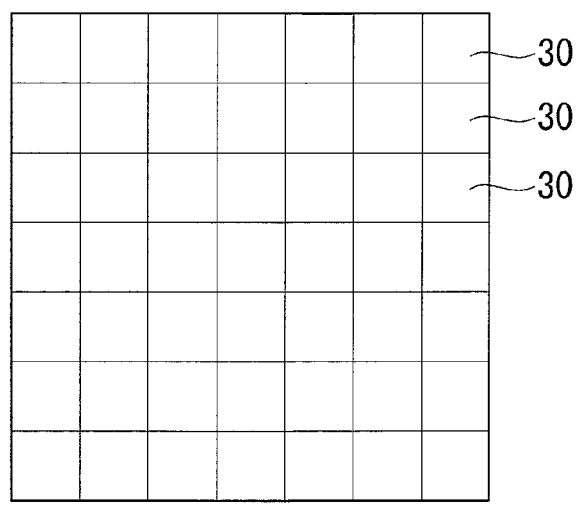
FIG. 2 is a schematic diagram showing a detector array in FIG. 1.

As the detector array 29, it is possible to use, for example, a CMOS (Complementary Metal Oxide Semiconductor) image sensor or a CCD image sensor. As shown in FIG. 2, this detector array 29 has, for example, an odd number of (7×7) minute detector elements (detector elements) 30 arrayed two-dimensionally.

These minute detector elements 30 are disposed at a position that is optically conjugate with the focal position of the objective lens 25. The minute detector elements 30 subdivide and detect the incident confocal spot of the fluorescence, perform photoelectric conversion of the detected fluorescence, and output light intensity signals serving as image information of the specimen S.

Figure 3:
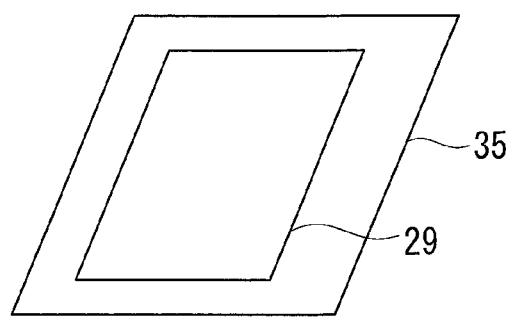
FIG. 3 is a schematic diagram showing the detector array and a motorized stage in FIG. 1.
Figure 3:
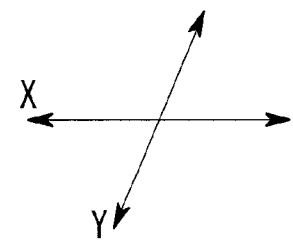

This detector array 29, which is supported by a motorized stage 35, as shown in FIG. 3, is configured so that its positions in the X-direction and the Y-direction can be shifted by means of the motorized stage 35. The motorized stage 35 is driven by, for example, a motor or a piezoelectric device, which is not illustrated.

The superresolution calculating portion 31 measures the intensity distribution of the confocal spot of the fluorescence incident on the detector array 29, on the basis of the light intensity signal output from each of the minute detector elements 30 in the detector array 29, and calculates the peak position in the intensity distribution, in other words, the center position of the confocal spot.

For example, the superresolution calculating portion 31 compares the light intensity signal from each minute detector element 30 and determines that the center position of the confocal spot of the fluorescence is located at the minute detector element 30 where the fluorescence intensity is highest.

The controller 33 operates the Ar laser device 1A, the HeNe-G laser device 1B, or the HeNe—R laser device 10 in the laser unit 10 so as to selectively emit, by using the acousto-optic element 9, the laser beams generated therein. The controller 33 performs scanning driving of the X and Y galvanometer mirrors 17A and 17B so as to scan the laser beam during the swiveling operation of the X and Y galvanometer mirrors 17A and 17B.

The controller 33 individually switches the minute detector elements 30 ON/OFF so as to select the region which is turned ON. By performing X and Y driving of the motorized stage 35, the controller 33 shifts the positions of the detector array 29 in the X-direction and the Y-direction relative to the position of the confocal spot of the fluorescence.

Thus, in accordance with the center position of the confocal spot of the fluorescence, which is calculated by the superresolution calculating portion 31, the controller 33 adjusts the X-direction and Y-direction positions of the detector array 29 so that the center position of the confocal spot of the fluorescence and the center position of the detector array 29 are aligned.

In addition, the controller 33 sums the light intensity signals of fluorescence coming from the same position on the specimen, which are detected by different minute detector elements 30 at different detection timings in accordance with the scanning of the laser beam by the galvanometer scanner 17. Then, the controller 33 creates an image of the specimen S by arraying the summed pixel values in association with the scanning position of the galvanometer scanner 17.

The operation of the thus-configured scanning laser microscope 100 will now be described.

To observe the specimen S with the scanning laser microscope 100 according to this embodiment, first, the positional relationship between the confocal spot of the fluorescence incident on the detector array 29 and the individual minute detector elements 30 in the detector array 29 is adjusted. In this case, a fluorescent marker is applied to the specimen S, and the acousto-optic element 9 and the detector array 29 are operated by the controller 33.

For example, a command for selecting the Ar laser device 1A is output to the acousto-optic element 9 in the laser unit 10 by the controller 33. Then, the laser beam with the excitation wavelength of 488 nm output from the Ar laser device 1A is selected by the acousto-optic element 9 and is emitted from the laser unit 10.

The laser beam with an excitation wavelength of 488 nm emitted from the laser unit 10 propagates through the single-mode fiber 11 and is guided to the collimator lens 13. Then, the laser beam is shaped into a collimated beam by the collimator lens 13 and is reflected by the excitation dichroic mirror 15A. The laser beam reflected by the excitation dichroic mirror 15A passes through the pupil projection lens 19, via the galvanometer scanner 17, is reflected at the reflecting mirror 21, and is imaged in the form of a spot on the specimen S via the image-forming lens 23 and the objective lens 25.

Fluorescence with a center wavelength of, for example, 520 nm, is generated when the fluorescent marker is excited due to the laser beam spot forming an image, whereupon the fluorescence is collected by the objective lens 25 and returns along the light path of the laser beam. Then, the fluorescence passes through the excitation dichroic mirror 15A, via the image-forming lens 23, the reflecting mirror 21, the pupil projection lens 19, and the galvanometer scanner 17, is focused by the confocal lens 27, and is incident on the detector array 29.

In the detector array 29, the confocal spot of the fluorescence projected by the confocal lens 27 is subdivided and detected by the plurality of minute detector elements 30, the fluorescence detected at each of the minute detector elements 30 is photoelectrically converted, and the light intensity signal serving as the image information is output.

The light intensity signals output from the respective minute detector elements 30 are sent to the superresolution calculating portion 31 via the controller 33 and are compared with each other by the superresolution calculating portion 31. Then, the minute detector element 30 at which the fluorescence intensity is highest is detected, and the center position of the confocal spot of the fluorescence is calculated from the position of that minute detector element 30 by the superresolution calculating portion 31.

Figure 4:
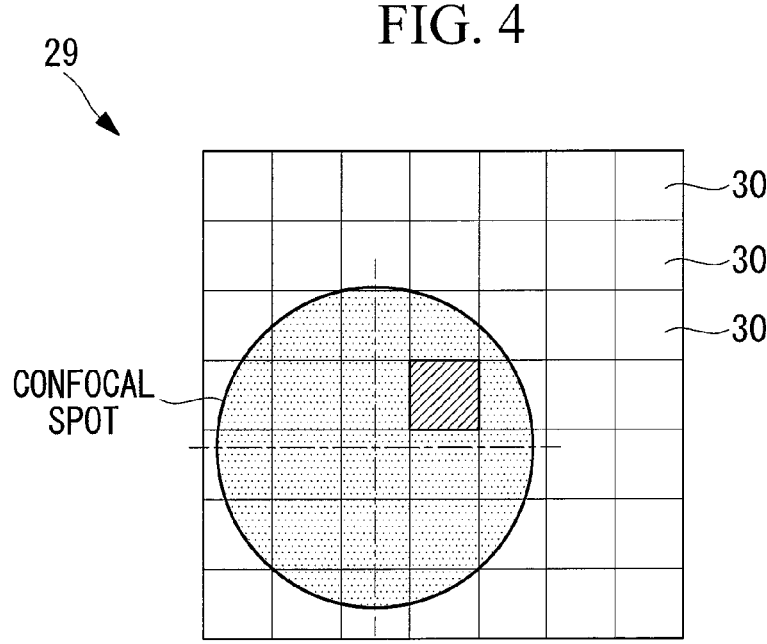
FIG. 4 is a diagram showing a state in which the position of a spot of fluorescence and the position of a minute detector element are misaligned.

Next, as shown in FIG. 4, for example, in the case where the center position of the confocal spot of the fluorescence, which is calculated by the superresolution calculating portion 31, is shifted from the minute detector element 30 located at the center of the detector array 29, the motorized stage 35 is driven in the X and Y directions by the controller 33 so that the center position of the confocal spot of the fluorescence and the position of the minute detector element 30 at the center of the detector array 29 are aligned.

Figure 5:
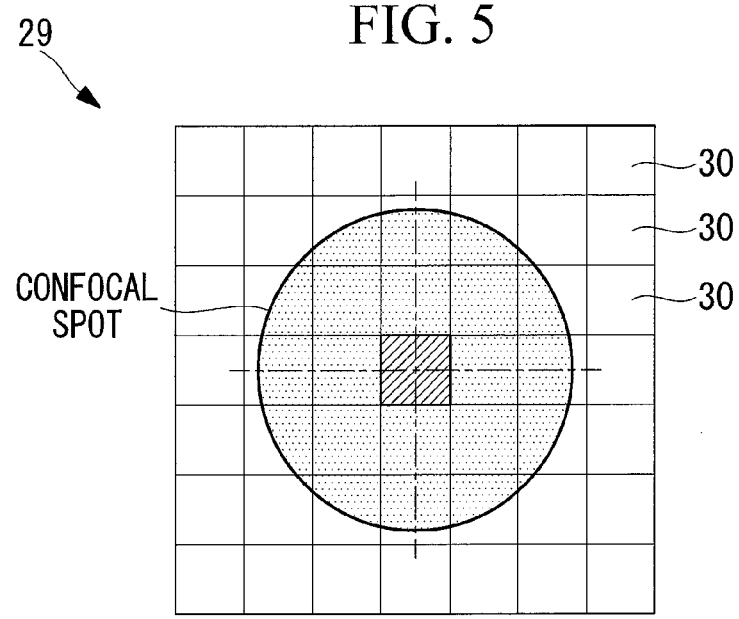
FIG. 5 is a diagram showing a state in which the position of the spot of fluorescence and the position of the minute detector element are aligned.

By driving the motorized stage 35, as shown in FIG. 5, the positions of the detector array 29 in the X-direction and the Y-direction are adjusted so that the center position of the confocal spot of the fluorescence moves to the minute detector element 30 at the center of the detector array 29. By doing so, the confocal spot of the fluorescence and the minute detector elements in the array detector 29 are positionally aligned.

Once positional alignment of the confocal spot of the fluorescence and the minute detector elements 30 in the detector array 29 has been completed, the laser beam is scanned to create an image of the specimen S. In this case, the galvanometer scanner 17 is operated by the controller 33, and the laser beam emitted from the laser unit 10 is deflected by the galvanometer scanner 17 so as to be two-dimensionally scanned on the specimen S.

By operating the galvanometer scanner 17, the light spot imaged on the specimen S is scanned in the horizontal direction by the X galvanometer mirror 17A, is then scanned by a distance corresponding to one pixel in the vertical direction by the Y galvanometer mirror 17B, and is scanned again in the horizontal direction by the X galvanometer mirror 17A, and this sequence repeats.

Next, the confocal spot of the fluorescence that is generated in the specimen S by scanning it with the laser beam and that is incident on the detector array 29 is subdivided and detected by the plurality of minute detector elements 30. By doing so, the fluorescence coming from the same position on the specimen is detected by different minute detector elements 30 at different detection timings in accordance with the scanning of the laser beam.

Next, light intensity signals of the fluorescence coming from the same position on the specimen, which are detected by different minute detector elements 30 at different detection timings in accordance with the scanning of the laser beam, are summed, and the summed pixel values are arrayed in association with the scanning position of the galvanometer scanner 17. As a result, the confocal pinhole is virtually reduced in size, and it is possible to create an image with improved resolution. By doing so, the user can observe the specimen S with superior precision based on a superresolution image of the specimen S.

As described above, with the scanning laser microscope 100 according to this embodiment, by adjusting the positions of the detector array 29 in the X and Y directions so that the center position of the confocal spot of the fluorescence incident on the detector array 29 is aligned with the center position of the detector array 29, it is possible to positionally align the confocal spot of the fluorescence and each of the minute detector elements 30 in the detector array 29 in a straightforward manner.

By doing so, even if the positional relationship between the confocal spot of the fluorescence and the minute detector elements 30 were to become misaligned, the position of the confocal spot of the fluorescence and the position of the minute detector elements 30 can be easily aligned, making it possible to create an image having the expected superresolution effect in a straightforward manner and with superior precision.

Since the detector array 29 has an odd number of minute detector elements 30, the minute detector elements 30 can be positioned two-dimensionally with any one minute detector element 30 at the center, and the center position of the confocal spot of the fluorescence can be aligned with the position of the single minute detector element 30 located at the center of the detector array 29. By doing so, it is possible to obtain light intensity signals with high precision compared with a case where the center position of the confocal spot of the fluorescence straddles the positions of a plurality of the minute detector elements 30.

As a modification of this embodiment, if, for example, optical elements such as the excitation dichroic mirrors 15A, 15B, and 15C and the objective lens 25, or the wavelengths etc. of the laser beams generated in the laser unit 10 are changed, preferably, the superresolution calculating portion 31 calculates the center position of the confocal spot of the fluorescence, and the positions of the detector array 29 in the X and Y directions are adjusted by the controller 33 on the basis of the center position of the confocal spot of the fluorescence.

If the excitation dichroic mirrors 15A, 15B, and 15C and the objective lens 25 are changed or if the wavelengths of the laser beams are changed, the positional relationship between the confocal spot of the fluorescence and the minute detector elements 30 may become misaligned. To deal with this, with this modification, if the objective lens 25 etc. or the wavelengths of the laser beams are changed, the center position of the confocal spot of the fluorescence can be automatically calculated by the superresolution calculating portion 31, and the position of the confocal spot of the fluorescence and the positions of the minute detector elements 30 can be aligned by the controller 33. Therefore, it is possible to create an image having the expected superresolution effect in a straightforward manner and with superior precision.

In this embodiment, although it has been assumed that the positions of the detector array 29 in the X-direction and the Y-direction are adjusted, instead of this, for example, the selection range of the minute detector elements 30 to be turned ON may be adjusted by the controller 33. In this case, the selection range of the minute detector elements 30 to be turned ON should be adjusted by the controller 33 so that the center position of the confocal spot of the fluorescence calculated by the superresolution calculating portion 31 is aligned with the position of the minute detector element 30 at the center of the selection range.

In this embodiment, it has been assumed that the superresolution calculating portion 31 determines that the center position of the confocal spot of the fluorescence is located at the minute detector element 30 at which the fluorescence intensity is highest. Instead of this, for example, the superresolution calculating portion 31 may calculate a weighted average of the intensity distribution in the confocal spot of the fluorescence and may determine that the center position of the confocal spot of the fluorescence is located at the corresponding minute detector element 30.

In addition, the superresolution calculating portion 31 may store, in advance, an intensity distribution of the confocal spot of the fluorescence and may derive the center position of the confocal spot of the fluorescence by comparing it against the intensity distribution at each of the minute detector elements 30. By doing so, the center position of the confocal spot of the fluorescence can be estimated more finely than the unit size of the minute detector elements, and thus, the confocal spot of the fluorescence and the minute detector elements 30 in the detector array 29 can be positionally aligned with higher precision.

Second Embodiment

Next, a scanning laser microscope according to a second embodiment of the present invention will be described with reference to the drawings.

Figure 6:
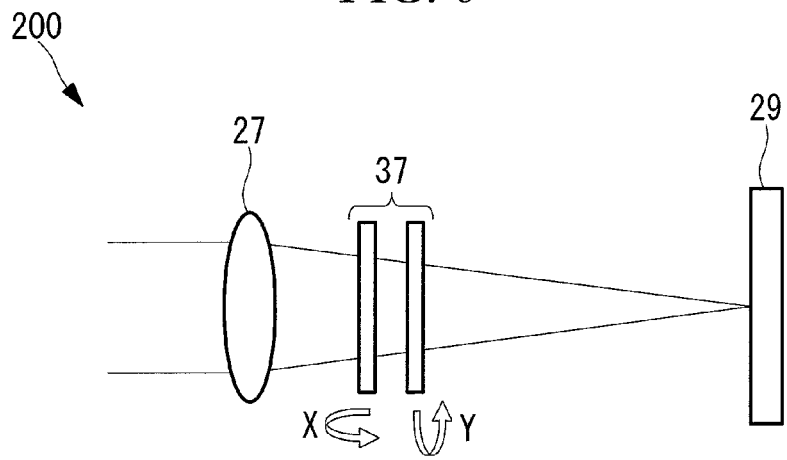
FIG. 6 is a diagram showing a beam-deflecting plate in a scanning laser microscope according to a second embodiment of the present invention.

As shown in FIG. 6, a scanning laser microscope 200 according to this embodiment differs from the first embodiment in that beam-deflecting plates (parallel-sided flat glass plates) 37 formed of glass plates are provided, and the confocal spot of the fluorescence and the detector array 29 are moved relative to each other by controlling the beam-deflecting plates 37.

In the following, portions having the same configuration as those in the scanning laser microscope 100 according to the first embodiment are assigned the same reference signs, and a description thereof is omitted.

The beam-deflecting plates 37 are formed of a pair of glass plates having a uniform constant thickness, which are disposed parallel to each other in the plate thickness direction with a gap therebetween. The beam-deflecting plates 37 are disposed in the light path between the confocal lens 27 and the detector array 29.

These beam-deflecting plates 37 are designed, for example, so that it is possible to change their angles about the X-axis and the Y-axis by means of motors (not illustrated). Also, the beam-deflecting plates 37 are designed so as to be capable of translating the fluorescence passing therethrough according to the angle of incidence, by changing the angle of incidence of the fluorescence.

The controller 33 is configured so as to shift the positions of the confocal spot of the fluorescence made incident on the detector array 29 in the X-direction and the Y-direction by changing the angles of the beam-deflecting plates 37 about the X-axis and the Y-axis to change the angle of incidence of the fluorescence.

Then, according to the center positions of the confocal spot of the fluorescence, which are calculated by the superresolution calculating portion 31, the controller 33 adjusts the angles of the beam-deflecting plates 37 about the X-axis and the Y-axis so that the center position of the confocal spot of the fluorescence and the center position of the detector array 29 become aligned.

With such a configuration, when the center position of the confocal spot of the fluorescence incident on the detector array 29 is shifted from the minute detector element 30 located at the center of the detector array 29, the motors of the beam-deflecting plates 37 are driven by the controller 33 so that the center position of the confocal spot of the fluorescence calculated by the superresolution calculating portion 31 and the position of the minute detector element 30 at the center of the detector array 29 become aligned.

Accordingly, the angles of the beam-deflecting plates 37 about the X-axis and the Y-axis are adjusted so that the center position of the confocal spot of the fluorescence moves to the minute detector element 30 at the center of the detector array 29, and the confocal spot of the fluorescence and the minute detector elements 30 in the detector array 29 thus become positionally aligned.

Therefore, with the scanning laser microscope 200 according to this embodiment, the confocal spot of the fluorescence incident on the detector array 29 is moved simply by changing the angles of the beam-deflecting plates 37 using the controller 33, and thus, it is possible to easily align the center position of the confocal spot of the fluorescence and the center position of the detector array 29.

In this embodiment, it is preferable to correct aberrations in the beam-deflecting plate 37 in advance. By doing so, even if the shape of the fluorescence changes slightly due to non-spherical aberrations in the beam-deflecting plates 37, the influence of such aberrations can be avoided.

Third Embodiment

Next, a scanning laser microscope according to a third embodiment of the present invention will be described with reference to the drawings.

Figure 7:
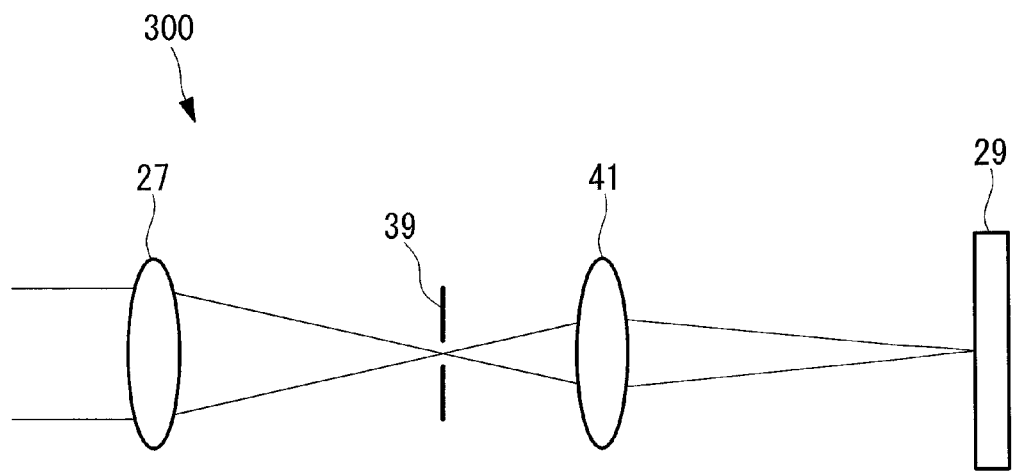
FIG. 7 is a diagram showing a confocal pinhole in a scanning laser microscope according to a third embodiment of the present invention.

As shown in FIG. 7, a scanning laser microscope 300 according to this embodiment differs from that of the first embodiment in that it includes a confocal pinhole 39 that restricts the bundle of rays of the fluorescence collected by the confocal lens 27, and a reprojection lens 41 that converges the fluorescence passing through the confocal pinhole 39 to form an image and reprojects the confocal spot of the fluorescence onto the detector array 29.

In the following, portions having the same configuration as those in the scanning laser microscope 100 according to the first embodiment are assigned the same reference signs, and a description thereof will be omitted.

The confocal pinhole 39 is disposed at a position that is conjugate with the observation surface of the specimen S. The confocal pinhole 39 has an opening that is slightly larger than the confocal spot of the fluorescence projected at the focal position by the confocal lens 27 and is designed so that light such as stray light coming from outside the focal plane of the laser beam in the specimen S is blocked.

With the scanning laser microscope 300 configured in this way, after the fluorescence focused by the confocal lens 27 passes through the confocal pinhole 39, it is converged by the reprojection lens 41 and is incident on the detector array 29. Accordingly, light coming from outside the focal plane of the laser beam in the specimen S is blocked, and it is possible to create an image of the specimen S by detecting, with the individual minute detector elements 30, only the fluorescence generated in the focal plane of the laser beam in the specimen S, which is reprojected onto the detector array 29.

In this embodiment, the confocal spot of the fluorescence and the detector array 29 may be moved relative to each other by using the beam-deflecting plates 37, as in the second embodiment.

In addition, in this embodiment, it is also permissible that a plurality of confocal pinholes 39 having different opening diameters can be selectively disposed in the light path of the fluorescence by using a turret or the like (not illustrated). By doing so, it is possible to change the confocal pinhole 39 that is to be disposed in the light path in response to replacement of the objective lens 25 with another one or wavelength switching of the laser beam, thus allowing the imaging conditions to be optimized.

Although this embodiment employs a confocal pinhole 39, instead of this, as shown in FIG. 8 for example, it may employ an aperture 43 that has an opening slightly larger than the confocal spot of the fluorescence projected at the focal position by the confocal lens 27 and that blocks light such as stray light coming from outside the focal plane of the laser beam in the specimen S.

In this case, the aperture 43 should be disposed in the light path directly in front of the detector array 29. By doing so, with the aperture 43, it is possible to achieve an effect similar to that in the case where the confocal pinhole 39 is used. This embodiment is advantageous in cases where there is a difference in size between the aperture 43 and the detector array 29.

In this modification, it is preferable that the opening diameter of the aperture 43 be adjustable. By doing so, the opening diameter of the aperture 43 can be changed in response to replacement of the objective lens 25 with another one or wavelength switching of the laser beam, thus allowing the imaging conditions to be optimized.

Although the embodiments of the present invention have been described above in detail with reference to the drawings, the specific configuration is not restricted to these embodiments, and the present invention encompasses design modifications and so forth that do not depart from the scope of the invention. For example, the present invention is not limited to the forms applied to the embodiments described above and may be applied to embodiments in which these embodiments are appropriately combined; it is not particularly limited.

Each of the embodiments described above has been described for the case where the detector array 29, such as a CMOS image sensor or CCD image sensor, has been given as an example of the detector portion. Instead of this, for example, a multi-anode PMT (photomultiplier tube) having a plurality of detector elements, such as H8711 (4×4 detector elements) or H7546 (8×8 detector elements), both manufactured by Hamamatsu Photonics, K.K., may be employed. In the case where the detector portion has 3×3 or more detector elements, it is preferable to select the detector elements to be turned ON so that the detector elements that are made to detect the fluorescence are disposed in an approximately circular shape.

REFERENCE SIGNS LIST

1A Ar laser device (light source)
1B HeNe-G laser device (light source)
1C HeNe—R laser device (light source)
17 galvanometer scanner (scanning portion)
25 objective lens
29 detector array (detector portion)
30 minute detector element (detector element)
31 superresolution calculating portion (calculating portion)
33 controller
37 beam-deflecting plate (parallel-sided flat glass plate)
100, 200, 300 scanning laser microscope
S specimen

The invention claimed is:

1. A method for creating a superresolution image of a specimen using a scanning laser microscope comprising a scanner, a light source, an objective lens, and a detector array which has a plurality of minute detector elements arrayed two-dimensionally and disposed at a position that is optically conjugate with a focal position of the objective lens, the method comprising:
   scanning, with the scanner, a laser beam emitted from the light source on the specimen;
   radiating, with the objective lens, the laser beam scanned by the scanner onto the specimen and collecting, with the objective lens, return light coming from the specimen;
   projecting the return light coming from the specimen on the detector array which has the plurality of minute detector elements arrayed two-dimensionally and disposed at the position that is optically conjugate with the focal position of the objective lens;
   comparing outputs from the minute detector elements of the detector array and determining that a center position of a spot of the return light is disposed at the minute detector elements where an intensity of the return light is highest;
   moving a selection range of the detector array by selectively turning ON or OFF individual minute detector elements of the detector array, the minute detector elements which are turned ON defining the selection range, so that the center position of the spot is aligned with a center position of the selection range of the detector array; and
   creating the superresolution image of the specimen by summing light intensity signals of the return light coming from a same position on the specimen, which are detected by different minute detector elements at different detection timings in accordance with the scanning of the laser beam with the scanner.

2. The method according to claim 1, wherein the detector array has an odd number×odd number of the minute detector elements.

3. The method according to claim 1, wherein, in a case in which the objective lens or a wavelength of the laser beam changes, the center position of the spot of the return light is calculated.

* * * * *